United States Patent [19]

Yamasawa et al.

[11] Patent Number: 4,771,790
[45] Date of Patent: Sep. 20, 1988

[54] ELECTRONIC BLOOD PRESSURE METER

[75] Inventors: Tsutomu Yamasawa, Takatsuki; Kenichi Yamakoshi, Sapporo; Hideaki Shimazu, Tokyo, all of Japan

[73] Assignee: Omron Tateisi Electronics Co., Japan

[21] Appl. No.: 50,387

[22] Filed: May 18, 1987

Related U.S. Application Data

[62] Division of Ser. No. 850,819, Apr. 11, 1986.

[30] Foreign Application Priority Data

| Apr. 12, 1985 | [JP] | Japan | 60-78651 |
| Apr. 12, 1985 | [JP] | Japan | 60-78653 |
| Apr. 12, 1985 | [JP] | Japan | 60-78655 |
| Apr. 12, 1985 | [JP] | Japan | 60-78657 |
| Apr. 12, 1985 | [JP] | Japan | 60-78658 |

[51] Int. Cl.⁴ ............................................. A61B 5/02
[52] U.S. Cl. .................................. 128/686; 128/667
[58] Field of Search ......... 128/686, 667, 327, DIG. 20, 128/679–683

[56] References Cited

U.S. PATENT DOCUMENTS

| 3,610,235 | 5/1969 | Vagacs | 128/DIG. 20 X |
| 3,760,795 | 9/1973 | Adelhed | 128/686 |
| 4,331,155 | 5/1982 | Sacks | 128/686 |
| 4,593,692 | 6/1986 | Flowers | 128/686 X |
| 4,667,672 | 5/1987 | Romanowski | 128/686 X |

FOREIGN PATENT DOCUMENTS

| 2343183 | 5/1974 | Fed. Rep. of Germany | 128/686 |
| 2842337 | 4/1979 | Fed. Rep. of Germany | 128/686 |
| 3109822 | 9/1982 | Fed. Rep. of Germany | 128/686 |

OTHER PUBLICATIONS

Hammer, W. E., et al., "Blood Pressure Finger Cuff", IBM Technical Disclosure Bulletin, vol. 8, No. 4, Sep. 1965.

Primary Examiner—Francis J. Jaworski
Attorney, Agent, or Firm—Wegner & Bretschneider

[57] ABSTRACT

Disclosed is an electronic blood pressure meter which is adapted to measure blood pressure from a finger. A cuff for applying pressure to the finger comprises a plurality of chambers which are communicated to each other and, thereby, provides a sufficient flexibility to closely conform to the contour of the finger. A sensor for detecting pulse wave data may be conveniently place on the inner surface of the cuff and is adapted to detect the reflection of light by an artery. Further, an air buffer can increase the effective air volume of the cuff and can reduce the rate of the pressure drop of the air cuff for a given rate of air vent from the cuff. By deriving the pulse wave data and computing the systolic and diastolic blood pressure therefrom in the course of increasing the air pressure of the cuff, the discomfort to the patient whose blood pressure is to be measured can be substantially reduced.

6 Claims, 12 Drawing Sheets

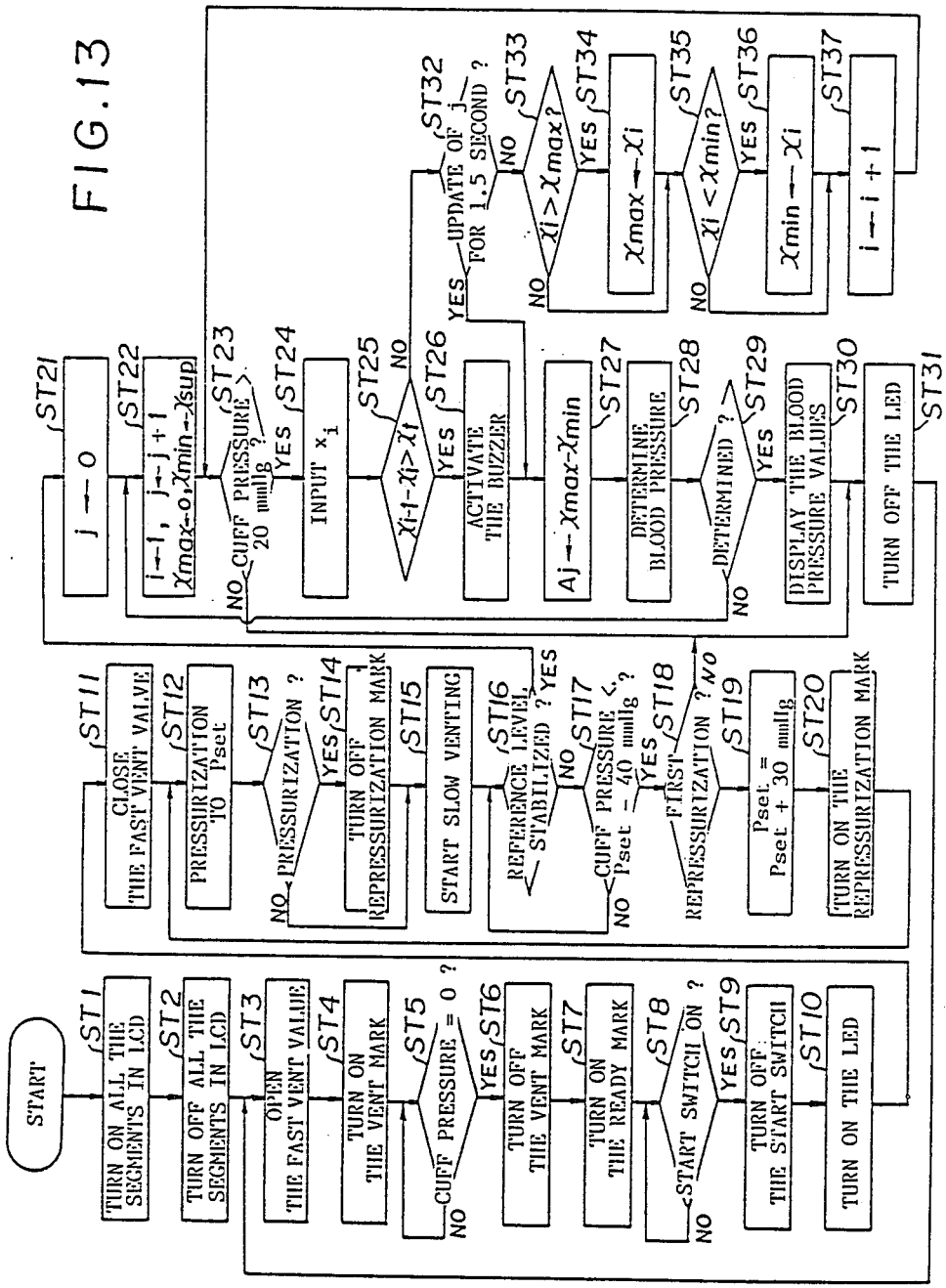

ELECTRONIC BLOOD PRESSURE METER

This application is a divisional of Ser. No. 850,819, filed Apr. 11, 1986.

TECHNICAL FIELD

The present invention relates to an electronic blood pressure meter for measuring the blood pressure of a living body by applying pressure to a part of the living body and detecting the resulting change in the volume of the artery and in particular to an electronic blood pressure meter which is adapted to measure the blood pressure of an artery of a finger of a living body.

BACKGROUND OF THE INVENTION

Conventional electronic blood pressure meters are mostly based on an indirect method in which a cuff is wrapped around an upper arm of a patient and pressurized to obstruct the blood flow in the upper arm, and the cuff pressures corresponding to the time points of appearance and disappearance of Korotkoff sound during the process of depressurizing the cuff are determined as the systolic (maximum) blood pressure and the diastolic (minimum) blood pressure, respectively.

An electronic blood pressure meter based on Riva-Rocci-Korotkoff method however has the disadvantage that since the Korotkoff sound is to be picked up by a microphone an accurate measurement of blood pressure is sometimes impossible particularly when the surrounding is noisy or when the cuff is rubbed by an object and the resulting sound is picked up by the microphone.

According to another method of measuring blood pressure or so-called oscillation method, the pulse wave produced in a living body in synchronization with the pumping motion of a heart is measured and blood pressure values are computed using the amplitude of the pulse wave as a parameter according to a certain algorithm.

Since this method does not require a microphone to pick up the pulse wave from an artery, the above-mentioned problems of the Riva-Rocci-Korotkoff method would not occur but the oscillation method still requires to apply a cuff to one's upper arm and it is quite cumbersome that the patient must roll up his sleeve for blood pressure measurement.

In view of such inconvenience of the prior art, the present inventors have realized that the above mentioned problems will be eliminated if an accurate blood pressure measurement can be performed on a part of a body which is normally exposed, such as a finger.

A certain device is known according to which water is used for pressing a finger for the purpose of measuring blood pressure from an artery in the finger, but a roller pump is necessary for the pressure control of the water which fills a cuff for the application or pressure to the finger and must be provided separate from the main unit, making it impossible to achieve a desired compactness of the structure.

Electronic blood pressure meters using air cuffs for pressurizing one's upper arm are well known in the art but an electronic blood pressure meter using such a cuff can not be directly applied to measuring blood pressure by one's finger since the volume of the cuff and the venting speed are excessive and the pressurization unit and, therefore, the signal processing unit of a conventional electronic blood pressure meter are unsuitable for this application.

For instance, a typical air cuff for a conventional blood pressure meter consists of a rectangular flexible air bag having an outer and an inner skin having the same dimensions and, therefore, when it is wrapped around one's arm and inflated by air pressure, the inner skin tends to develop creases or folds thereby causing uneven application of pressure to the upper arm. This tendency becomes more pronounced as the cuff is wrapped around an object having a smaller diameter such as a finger. Furthermore, the orientation of a sensor device attached to the inner skin tends to be unpredictable if such folds are produced in the vicinity of the sensor, thus reducing the reliability of the sensor.

In measuring blood pressure, it is necessary to detect the pulse wave of an artery but the artery in one's finger is so fine that a conventional pulse wave detector is not adequate for accurate detection. In a conventional pulse wave detector, as shown in FIG. 6, light emitted from a light emitting element L (for instance an LED) through an artery D in a finger F is received by a light sensitive element PT (for instance a photo transistor) and the pulse wave of the artery is detected as the changes of the intensity of the light received by the light sensitive element PT. According to this detector, since the light must pass through a distance corresponding to the width of the finger, it is difficult to achieve a desired sensitivity and the signal to noise ratio (SN ratio) of the signal detected by the light sensitive element PT tends to be low.

Another shortcoming of the above-mentioned conventional methods of measuring blood pressure is that since the measurement process takes place as the air pressure is gradually reduced and a substantial pressure must be built up in the cuff prior to starting the measurement the patient is subjected to a discomfort for a substantial time period.

BRIEF SUMMARY OF THE INVENTION

In view of such shortcomings of the prior art, a primary object of the present invention is to provide an electronic blood pressure meter which is accurate and easy to use.

Another object of the present invention is to provide an electronic blood pressure meter which is adapted to be used on a finger of a living body.

Yet another object of the present invention is to provide an electronic blood pressure meter which can achieve an extremely slow venting from a cuff so as to allow measurement of blood pressure by a finger of a living body.

Yet another object of the present invention is to provide an electronic blood pressure meter which can measure blood pressure as a cuff is being pressurized and thus can reduce the discomfort of the patient.

Yet another object of the present invention is to provide an advantageous air cuff for an electronic blood pressure meter which is adapted to be applied to a part of a living body having a relatively small diameter such as a finger.

Yet another object of the present invention is to provide an advantageous pulse wave detector for an electronic blood pressure meter which is highly sensitive and can achieve a high SN ratio.

According to a broad concept of the present invention, such objects are accomplished by providing an electronic blood pressure meter for measuring blood pressure, comprising: a cuff made of flexible material and defining an air chamber therein for applying air pressure to a finger inserted in a cylindrical space defined by an internal surface of the cuff; pressure control means connected to the air chamber defined in the cuff for varying the air pressure inside the cuff; a cuff pressure sensor for detecting the air pressure in the air chamber of the cuff; pulse wave information detecting means attached to the cuff for detecting pulse wave information as the air pressure in the air chamber of the cuff is varied; and blood pressure determination means for determining a blood pressure value from the cuff air pressure detected by the cuff pressure sensor and the pulse wave information detected by the pulse wave information detecting means.

According to a certain aspect of the present invention, the pressure control means comprises an air pump, a pressure sensor, a fast vent valve and a slow vent valve. And, additionally, an air buffer may be connected either directly or indirectly to the air cuff for the purpose of increasing the effective volume of the air cuff and reducing the rate of pressure drop in the air cuff for a given venting rate. By appropriate arrangement of these pressure control elements, it is possible to measure blood pressure values from the pulse wave data detected by the pulse wave detecting means either while the cuff pressure is being increased or while the cuff pressure is being reduced.

According to another aspect of the present invention there is provided a cuff for measuring blood pressure by surrounding a finger of a living body and obstructing the blood flow in the finger, comprising: an air bag having an internal and an external skin which have a certain length and a certain width sufficient for substantially surrounding the finger, the interior of the air bag defined by the two skins being divided into a plurality of air chambers, which are communicated with each other, along a circumferential direction of the air bag as it surrounds the finger, the internal skin of the air bag adjacent to the finger being substantially flexible at least along the longitudinal direction of the finger and being adapted to be inflated individually with respect to different parts of the internal skin which is adjacent to the finger defining different ones of the divided air chambers; a pulse wave sensor attached to the internal skin of the air bag; and a conduit provided in the air bag for supplying and venting air pressure into and from the air chambers.

It is particularly preferable if the inner skin is provided with a plurality of bulges of a substantially trapezoidal or semicircular shape defining the corresponding air chambers. Thereby, when the cuff is curved into a cylindrical shape, the top surfaces of the bulges define a cylindrical space for inserting a part of a living body such as a finger therein while the lateral side portions of the bulges cme closer together without interfering each other. As a result, a uniform contact between the air cuff and a part of a living body for instance a finger can be achieved and high measurement accuracy can be assured.

According to yet another aspect of the present invention, there is provided a pulse wave detector for detecting the pulsation of an artery in a living body; comprising: a light emitting element for emitting light onto an artery of a living body; and a light sensitive element for detecting the reflection of the light from the light emitting element and producing a signal representative of the light received by the light sensitive element. According to this aspect of the present invention, since the path of the light in the living body is generally shorter than that of the conventional pulse wave detector according to which light is transmitted through a living body for the detection of pulse waves, the attenuation of the light is less and higher detection sensitivity can be achieved.

BRIEF DESCRIPTION OF THE DRAWINGS

The present invention will now be shown and described in the following in terms of concrete embodiments thereof with reference to the appended drawings, in which:

FIG. 13 is a flow chart illustrating the action of a second embodiment of the electronic blood pressure meter according to the present invention;

DESCRIPTION OF THE PREFERRED EMBODIMENTS

Figure 1A:
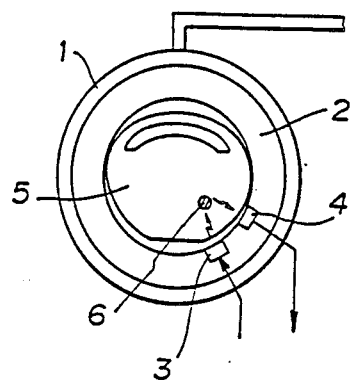
FIG. 1(a) is a sectional view of a cuff assembly according to the present invention illustrating how the pulse wave data can be obtained from an artery in a finger.
Figure 1B:
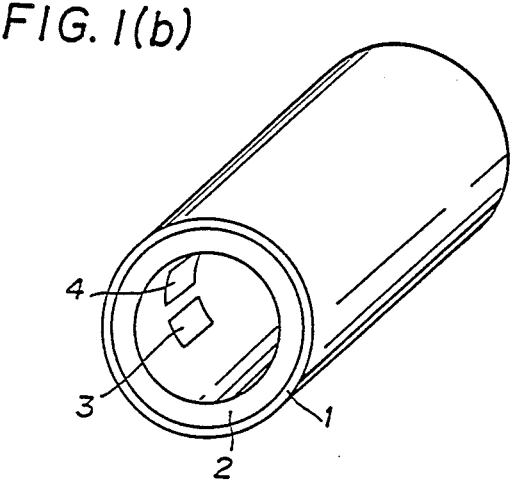
FIG. 1(b) is a perspective view of the cuff assembly of FIG. 1(a)

FIGS. 1a and 1b show an embodiment of a pulse wave detector which is installed in a cuff unit which will be described in greater detail hereinafter. As shown in these drawings, a substantially cylindrical cuff 2 is fitted into a tubular member 1 and a light emitting element 3 such as an LED and a light sensitive element 4 such as a photo transistor are attached, adjacent to each other, in the internal wall of the cuff 2 curved into a cylindrical shape.

As shown in FIG. 1a, a finger 5 is inserted in the interior of the cylindrical cuff 2 which is adapted to be pressed onto the finger 5 by being pressurized by an air pump in a manner which is described in greater detail hereinafter. The light from the light emitting element 3 is projected onto an artery 6 of the finger 5 and, after being reflected by the artery 6, reaches the light sensitive element 4. Therefore, the light sensitive element 4 can detect the pulse wave of the artery 6 as the changes in the intensity of the light received thereby while the cuff 2 is being pressurized or depressurized.

Figure 5A:
FIG. 5 is a wave form diagram comparing the outputs from a pulse wave detector according to the present invention and a conventional pulse wave detector.
Figure 5B:
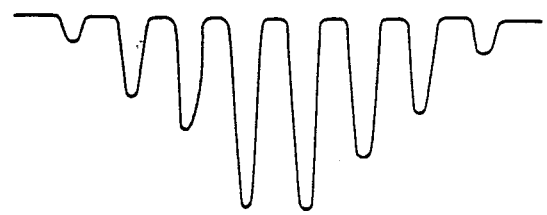
Figure 6:
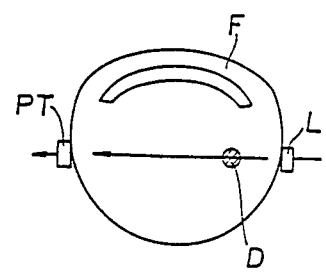
FIG. 6 is a schematic sectional view of an example of conventional pulse wave detector.

According to the illustrated embodiment, since the overall length of the light path between the light emitting element 3 and the light sensitive element 4 by way of the artery 6 is shorter than that of the prior art according to which the light passes through a finger as described earlier with reference to FIG. 6, the pulse wave level detected by the embodiment shown in FIGS. 1a and 1b is generally greater in amplitude than that described by the conventional pulse wave detector illustrated in FIG. 6 typically by a factor of 10 or higher and this difference is clearly indicated in the graph given in FIG. 5 in which (a) denotes the pulse wave level detected by the convention detector while (b) denotes the pulse wave level detected by the embodiment of the present invention.

Figure 2:
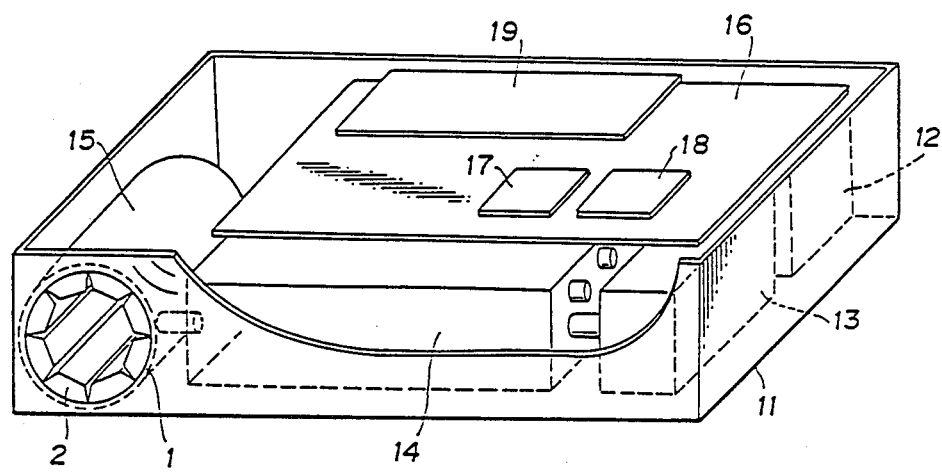
FIG. 2 is partially broken away perspective view of an embodiment of the electronic blood pressure meter according to the present invention.

FIG. 2 shows a partially broken away external view of an embodiment of the electronic blood pressure meter according to the present invention. A main body casing 11 accommodates a battery unit 12 located in a right hand rear portion thereof, an air pump 13 located in front of the battery unit 12, an air buffer 14 located substantially in the middle of the casing 11, and a cuff unit 15 located in a left hand portion of the casing 11. Further, a circuit board 16 extends over the top surfaces of the air buffer 14, the battery unit 12 and the air pump 13. A power switch 17, a start switch 18 and a liquid crystal display unit 19 are attached to the top surface of the circuit board 16 and appropriate electrical connections are made therebetween although it is not shown in the drawing. Also an MPU and other electronic component parts are mounted to the lower surface of the circuit board 16 and this is also not shown in the drawing.

Figure 3:
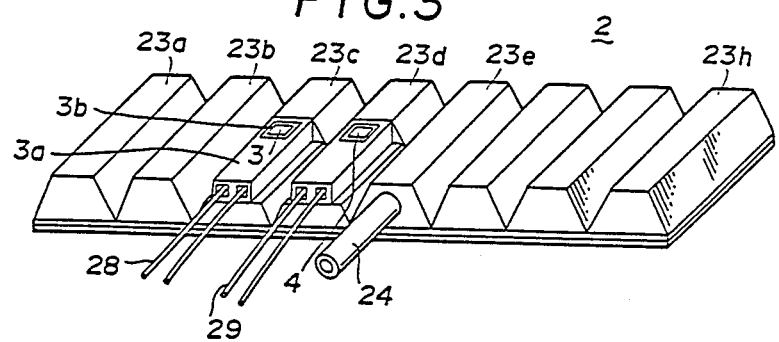
FIG. 3 is a perspective view of an embodiment of the cuff according to the present invention in its developed state.
Figure 7:
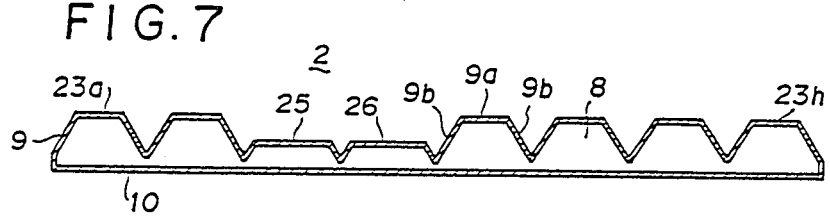
FIG. 7 is a sectional view of the cuff shown in FIG. 3.

The cuff unit 15 includes the tubular member 1 and the cuff 2 which were described earlier with reference to FIGS. 1a and 1b. As shown in FIGS. 3 and 7, the cuff 2 comprises an upper skin 9 and a lower skin 10 defining a chamber therebetween and these skins may also be called as an internal skin and an external skin because of their positions when the cuff is curved into the cylindrical shape shown in FIGS. 1a, 1b and 2. The space defined between the two skins 9 and 10 are divided into a plurality of air chambers 8, which are communicated to each other, with the internal skin 9 formed with so many bulges 23a to 23h which have a relatively small width and extend substantially the whole length of the cuff 2. An air tube 24 is connected to an end surface of one of the bulges 23e for supplying and venting air into and from the air chambers defined in the cuff 2.

Depressions 25 and 26 are formed in two of the protrusions 23c and 23d defining a pair of flat surfaces, and the light emitting element 3 and the light sensitive element 4 are mounted on these flat surfaces. The light emitting element 3 comprises a casing 3a made of synthetic resin which has a window on top surface thereof as shown in FIG. 3 for permitting therethrough the passage of light emitted from an LED (not shown in the drawings) received inside the casing 3a. The longitudinal external end portion the casing 3a is opened for passing thereinto a pair of lead wires 28 for the LED. The light sensitive element 4 has a similar structure which is likewise provided with a pair of lead wires 29 which are however connected to a photo transistor (not shown in the drawings) provided therein instead of the LED. The lead wires 28 and 29 leading out from these elements 3 and 4 are connected to the circuitry provided in the circuit board 16.

Thus, as described previously with reference to FIGS. 1a and 1b, the light emitted from the light emitting element 3 is projected onto an artery 6 in the finger 5 through the skin and the flesh of the finger 5 is reflected by the artery 6 back to the light sensitive element 4 again through the flesh and the skin of the finger 5 so that the pulse wave can be detected by the light sensitive element 4 as a variation of the intensity of the reflected light.

Figure 4:
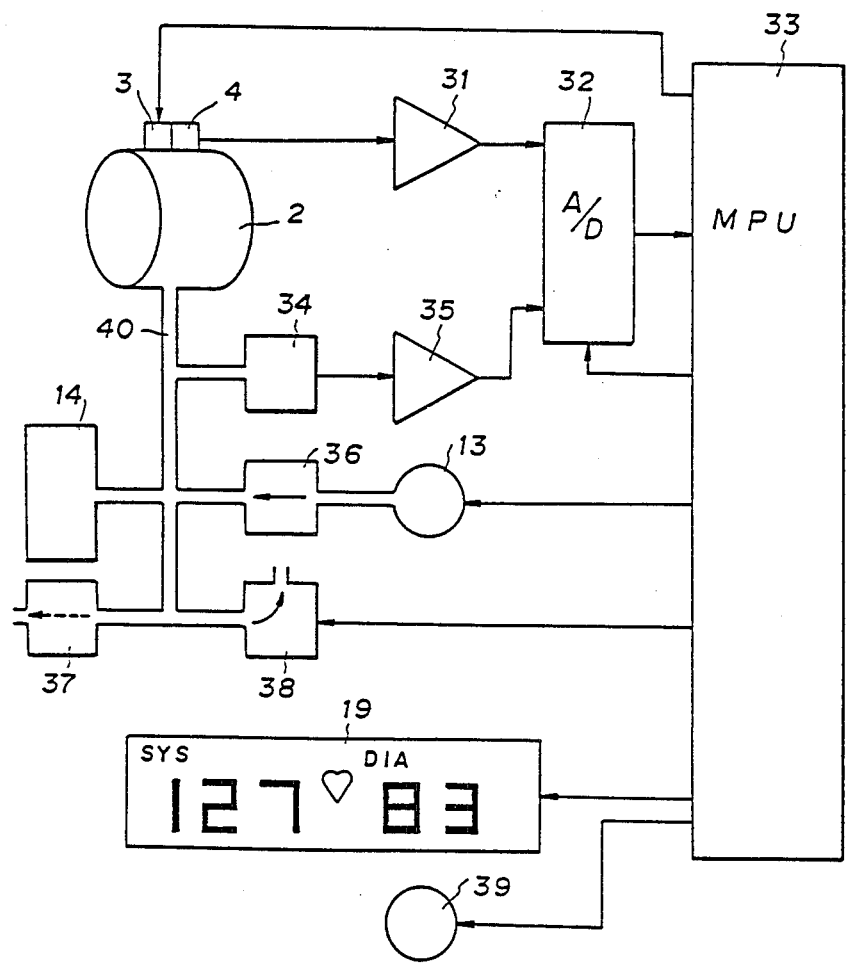
FIG. 4 is a schematic block diagram of a first embodiment of the electronic blood pressure meter according to the present invention.

FIG. 4 shows a functional block diagram of the first embodiment of the electronic blood pressure meter. As shown in this drawing, the light emitting element 3 deriving electric power from an MPU 33 is placed on the cuff 2 adjacent to the light sensitive element 4 whose output is supplied to the MPU 33 by way of an amplifier 31 and an AD converter 32. An air conduit 40 is connected to the cuff 2, and this air conduit 40 is connected to various forms of air control equipment operative to control the air pressure of the air cuff 2; i.e., a pressure sensor 34, an air buffer 14 or an air accumulator consisting of an air chamber of a certain volume, a slow vent valve 37 and a fast vent valve 38 which are directly connected to the conduit 40, and an air pump 13 whose output end is connected to the conduit 40 by way of one-way valve 36.

The cuff pressure signal detected by the pressure sensor 34 is amplified by an amplifier 35 and supplied to the MPU 33 by way of the AD converter 32. The MPU 33 is internally equipped with memory for storing a program and values derived during the process of arithmetic operations given by the program and, through appropriate switching of the AD converter 32, can perform the functions of inputting pulse wave data and cuff pressure data thereinto, turning on and off the air pump 13, opening and closing the fast vent valve 38, determining blood pressure from the pulse wave data, and indicating the status whether measurement is in progress or not.

The determined blood pressure values or the systolic blood pressure (SYS) and the diastolic blood pressure (DIA) are outputted from the MPU 33 and displayed on the display unit 19, and a buzzer 39 may be activated by a command from the MPU 33 at an appropriate timing as will be described hereinafter. The air buffer 14 has a certain volume which effectively increases the effective volume of the air cuff 2. Because of the presence of the air buffer 14, the drop in the pressure of the air cuff 2 is slower for a given rate of air venting as compared to the case in which the air buffer is not provided. As a result, even when a slow vent valve 37 for an arm cuff is applied to the present embodiment using the air cuff 2 for a finger, the pressure drop of the air cuff 2 is as slow as 2 to 3 mmHg/sec.

FIG. 7 shows the air cuff 2, used in the first embodiment of the present invention, in cross section. The outer skin 10 is made of relatively hard material but is flexible enough to be deformed from a flat shape to a cylindrical shape of a desired diameter. The inner skin 9 is made of flexible material such as rubber and formed with a plurality of bulges 23a to 23h (FIG. 3) which extend substantially the whole length of the cuff 2 and are arranged along the inner circumference of the cuff 2, when it is curved into the cylindrical shape, at substantially equal intervals. The circumferential edges of the inner skin 9 and the outer skin 10 are bonded together.

Each of the bulges 23a to 23h in the inner skin 9 has a substantially trapezoidal cross section and comprises a middle flat portion 9a and a pair of sloping portions 9b rising towards the lateral side edges of the middle flat portion 9a. Thus, a plurality of air chambers 8 are defined between the inner skin 9 and the outer skin 10 but they are communicated to each other. And the air tube 24 is connected to an end surface of the inner skin 9 (FIG. 3) for inflating and venting the cuff 2. Two of the bulges 23c and 23d are provided with the depressions 25 and 26 which define the flat surfaces for mounting the light emitting element 3 and the light receiving element 4 thereon as mentioned previously with reference to FIG. 3.

Thus, the cuff 2 is rolled into the cylindrical shape and fitted into the tubular member 1 in the electronic blood pressure meter. As a result, a cylindrical space is defined by the flat top portions 9a of the bulges 23a to 23h of the inner skin 9, and adjacent ones of the sloping portions 9b come close together without causing any substantial strain to the inner and outer skin 9 and 10. After a finger, for instance a first finger, is inserted into the thus defined cylindrical space and the cuff 2 is inflated through pressurized air supplied from the air tube 9 by turning on the power switch 17 and activating the air pump 13, the flat portions 9a of the bulges 23a to 23h of the inner skin 9 can conform to the contour of the finger 5 and will uniformly apply pressure to the finger 5.

Figure 8:
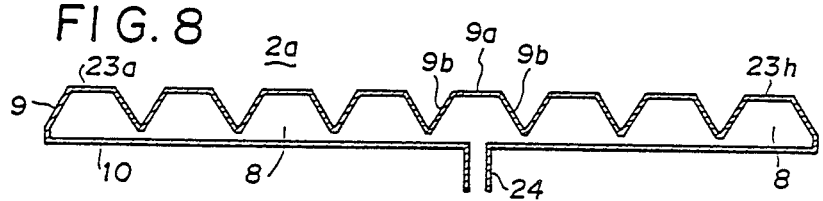
FIGS. 8 to 10 are sectional views similar to FIG. 7 showing different embodiments of the cuff according to the present invention.
Figure 9:
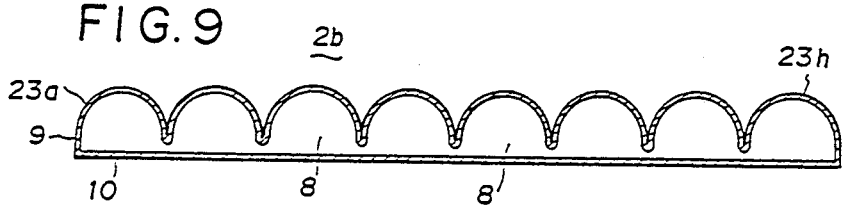
Figure 10:
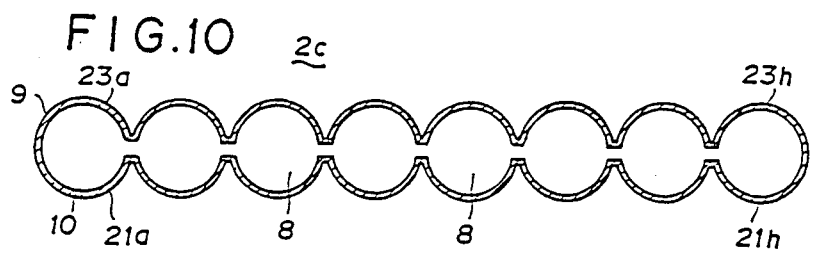

FIGS. 8 to 10 show different embodiments of the air cuff 2a to 2c according to the present invention. The embodiment shown in FIG. 8 is similar to the embodiment given in FIG. 7 but an air tube 24 is provided in the outer skin 10 instead of the inner skin 9. According to the embodiment given in FIG. 9, the bulges in the inner skin 9 are semi circular in cross section, as opposed to the trapezoidal shape of the previous embodiments, while the inner skin 10 is flat in the same manner as the previous embodiment. As a result, the air chambers 8 have semi circular cross sections. According to the embodiment given in FIG. 10, not only the inner skin 9 is provided with bulges similar to those of the embodiment of FIG. 9, but also the outer skin 10 is provided with similar bulges 21a to 21h in alignment with the corresponding bulges of the inner skin 9. Therefore, the air chambers 8 in this case are substantially circular in cross section.

Figure 11:
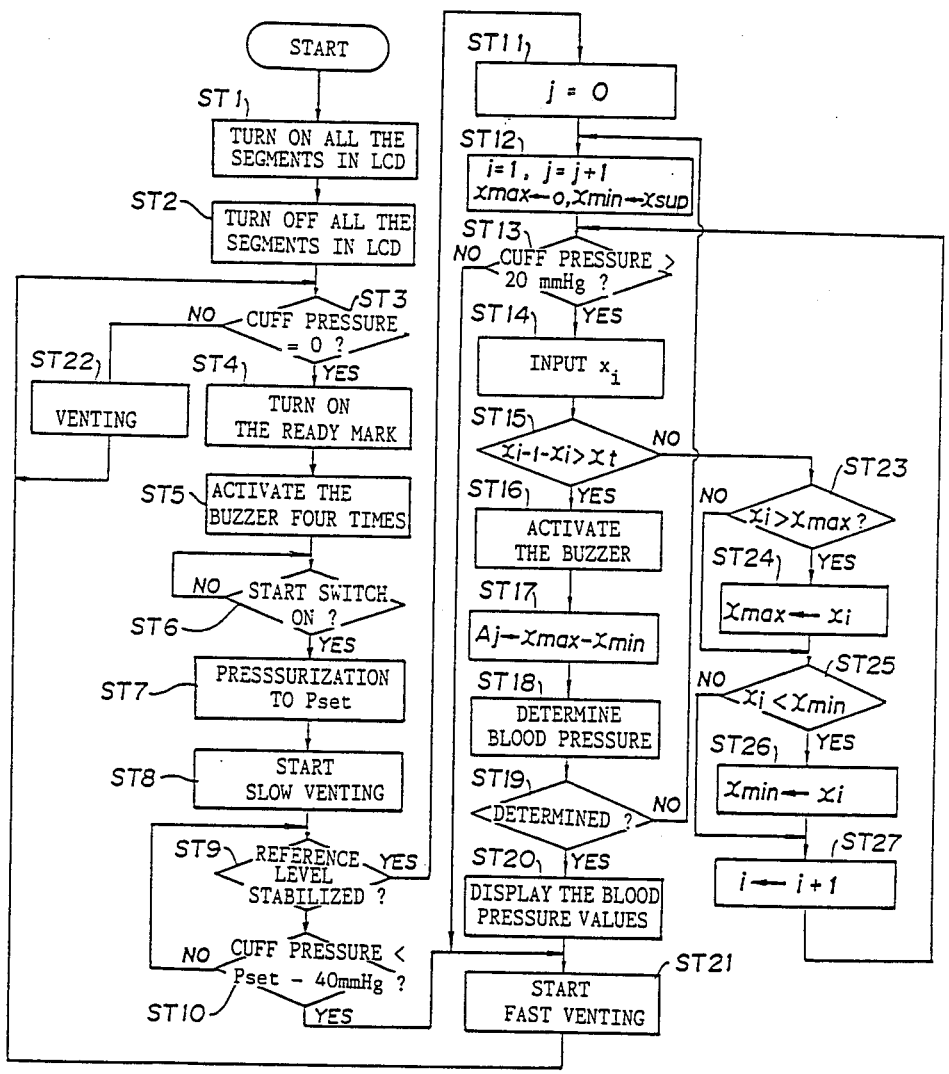
FIG. 11 is a flow chart illustrating the action of the first embodiment of the electronic blood pressure meter according to the present invention.

Now the action of the first embodiment of the electronic blood pressure meter is described in the following particularly with reference to the flow chart given in FIG. 11.

Prior to starting a measurement process, a patient puts his first finger of his left hand into the cylindrical space of the cuff 2, and the power switch 17 is turned on. This starts off the execution of the program stored in the memory of the MPU 33 and performs a segment check for the display unit 14 by turning on all the segments in the display unit 14 for 1.5 seconds in step 1. Thereafter, all the segments are turned off in step 2. In step 3, it is determined whether the cuff pressure is zero or not. If the cuff pressure is not zero, the fast vent valve 10 is activated in step 22 and the system flow returns to step 3. And, this is repeated until the cuff is sufficiently deflated. When the cuff pressure is zero in step 3, a ready mark (indicated as a heart shaped mark in the display unit 19 as shown in FIG. 4) is turned on in step 4 and the buzzer 15 is activated for four consecutive short time intervals in step 5. This completes the preparation of the electronic blood pressure meter for the actual measurement process.

At this instance, if the start switch 18 is turned on, the determination result of step 6 becomes yes, and the air pump 13 is activated. In step 7, the air pressurized by the air pump 13 is conducted to the main conduit 40 by way of the one-way valve 36 and is supplied to the air buffer 14 and the cuff 2 until the air pressure detected by the air pressure sensor 34 reaches a certain value $P_{set}$ programmed in the MPU 33. Typically, the value $P_{set}$ programmed in the MPU 33 is higher than the expected systolic blood pressure by 20 to 30 mmHg. Then, the air pump 13 is deactivated and venting from the cuff 2 takes place only through the slow vent valve 37 in step 8. However, since the reference level for pulse wave detection may not be stable immediately after the completion of the pressurization of the cuff 2, a stabilization process is conducted in steps 9 and 10. It is determined in step 9 whether the reference level is stable or not. If not, it is determined whether the pressure level is below the predetermined by value by more than 40 mmHg or not. If so, the cuff is rapidly vented by the fast vent valve 38 in step 21 and the process flow returns to step 3. If the pressure is not lower than the predetermined value by more than 40 mmHg, the process flow returns to step 9. Once the reference level for pulse wave detection has been stabilized, the amplitude of the pulse wave is determined in the subsequent steps.

In step 11 a pulse wave number j corresponding to the part of the pulse wave at which the amplitude is to be determined is set to zero. In step 12 the count of a sample counter for one cycle of pulse beat is reset to 1 and the pulse wave number is incremented by one. At the same time, a maximum pulse wave level $x_{max}$ is set to zero and a minimum pulse wave level $x_{min}$ is set to an upper limit value $x_{sup}$ which is higher than a conceivable maximum value of the pulse wave level.

In step 13, it is determined whether the cuff pressure is higher than 20 mmHg or not. If the cuff pressure is lower than 20 mmHg, the process flow advances to step 21 and rapid venting of the cuff 2 takes place. If the cuff pressure is higher than 20 mmHg, pulse wave data $x_1$ is inputted in step 14 and the difference between the current value of the pulse wave data $x_i$ and the previous value of the pulse wave data $x_{i-1}$ are compared with a certain value $x_t$ in step 15. In step 15 it is determined if this difference is greater than this certain value $x_t$ or not.

If the determination result of step 15 is negative, the process flow advances to step 23 and the current value of the pulse wave data $x_i$ is compared with the maximum pulse wave level $x_{max}$. If $x_i > x_{max}$ the maximum pulse wave level $x_{max}$ is updated by the value of $x_i$ in step 24. Conversely, if $x_i < x_{max}$ step 24 is skipped and the process flow advances to step 25. In step 25 the current pulse wave data $x_i$ is compared with the minimum pulse wave level $x_{min}$. If $x_i < x_{min}$ the minimum pulse wave level $x_{min}$ is updated by the value of $x_i$ in step 16. Conversely, if $x_i > x_{min}$ step 26 is skipped and the process flow advances to step 27.

When the updating of the maximum and minimum pressure level $x_{max}$ and $x_{min}$ in steps 23 to 26 is completed, the count i is incremented by one in step 27 and the process flow returns to step 13. Thereafter, steps 23 to 27 and steps 13 to 15 are repeated and the updating of the maximum and minimum pulse wave level $x_{max}$ and $x_{min}$ continues until $x_{i-1} - x_i > x_t$ or until the next cycle of pulse beat begins.

If it is determined that $x_{i-1} - x_i > x_t$ in step 15, the buzzer 39 is activated in step 16 and extraction of the pulse wave is notified to the user. Then, the difference between the maximum and minimum pulse wave level $x_{max}$ and $x_{min}$ (the amplitude of the pulse wave) $A_j$ is derived in step 17 and stored in the MPU 33. And a blood pressure determination process is conducted in step 18 using this amplitude $A_j$ as a parameter.

Figure 12A:
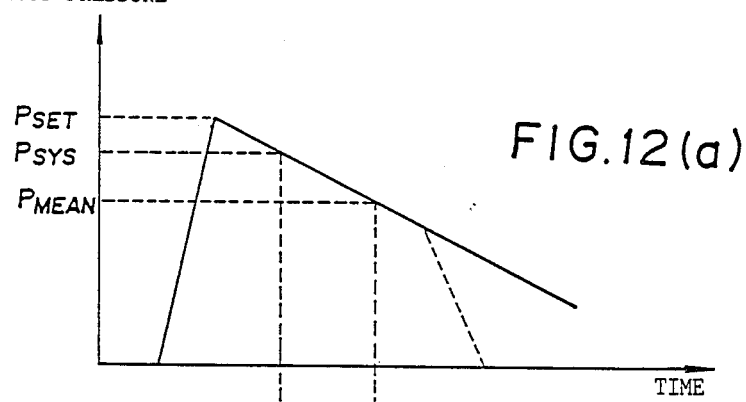
Figure 12B:
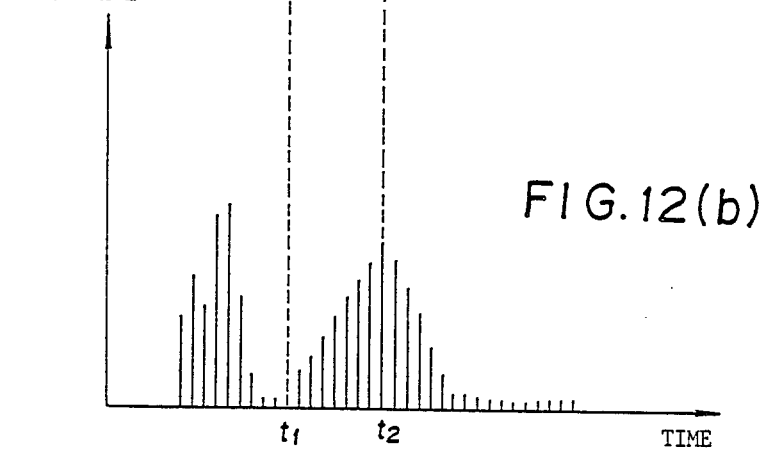

It is possible to determine blood pressure in a number of ways and, according to the present embodiment, the cuff pressure at the time point $t_1$ at which the pulse wave starts appearing is determined as the systolic blood pressure $P_{sys}$ (refer to FIG. 12) and the cuff pressure at the time point $t_2$ at which the amplitude of the pulse wave $A_j$ maximizes is determined as the average blood pressure $P_{mean}$. And the diastolic blood pressure $P_{dia}$ is determined by the following equation:

$$P_{mean} = P_{dia} + (P_{sys} - P_{dia})/3$$

And, until the diastolic blood pressure $P_{dia}$ is determined, the process flow continues returning from step 19 to step 12 and, after incrementing the pulse wave number j by one in step 12, the blood pressure determination process is continued by deriving the difference between the maximum and minimum pulse wave level $x_{max}$ and $x_{min}$ or the amplitude of the pulse wave) $A_j$.

Upon completion of the determination of the the maximum and minimum pressure level (step 19), these blood pressure values are displayed on the display unit 19 in step 20 and, thereafter, the fast vent valve 38 is activated in step 21 to complete the measurement process.

FIG. 13 is a flow chart illustrating the action of another embodiment of the electronic blood pressure meter of the present invention. According to the present embodiment, steps 1 and 2 are identical to steps 1 and 2 of the previous embodiment, but the fast vent valve 38 is activated or opened in step 3 and the fast vent mark is displayed in the display unit 19 in step 4 although it is not shown in the drawings. In step 5, it is determined whether the cuff pressure is zero or not and the process flow goes into a loop until the cuff pressure drops to zero.

When the cuff pressure has dropped to zero, the fast vent mark is turned off in step 6 and a ready mark (indicated as a heart shaped mark in the display unit 19 shown in FIG. 4) is turned on in step 7. Then, the user can know that the electronic blood pressure meter is ready for measurement. Here, by turning on the start switch 18, the process flow advances from step 8 to step 9 and an LED on the display unit 19 (not shown in the drawings) for indicating that a measurement process is in progress is lighted in step 10. Further, the fast vent valve 38 is closed in step 11 followed by the activation of the air pump 13, and the pressurization of the cuff 2 by the air pump 13 is continued until the cuff pressure reaches a certain pressure $P_{set}$ in step 12.

If this pressurization is determined as being a repressurization process for resuming a pressurization after an interruption of a pressurization in step 13 as is described hereinafter, and a repressurization mark which is described hereinafter is turned off in step 14. In either case, upon completion of the pressurization process, a slow venting is started in step 15. As mentioned previously, this venting process may be performed at the rate of 2 to 3 mmHg/sec. Thereafter, the process flow goes into a loop by way of steps 16 and 17 until the reference level for pulse wave detection is stabilized. If the cuff pressure has dropped below the predetermined pressure $P_{set}$ by more than 30 mmHg during this process, the repressurization mark is displayed on the display unit 19 in step 20 although it is not shown in the drawings and the system flow returns to step 12 for repressurization of the cuff 2.

At any rate, when it is determined in step 16 that the reference level for the pulse wave detection has been stabilized, the process flow advances to step 21. In step 21 a pulse wave number j corresponding to the part of the pulse wave at which the amplitude is to be determined is set to zero. In step 22 the count of a sample counter for one cycle of pulse beat is reset to 1 and the pulse wave number is incremented by one. At the same time, a maximum pulse wave level $x_{max}$ is set to zero and a minimum pulse wave level $x_{min}$ is set to an upper limit value $x_{sup}$ which is higher than a conceivable maximum value of the pulse wave level.

In step 23, it is determined whether the cuff pressure is higher than 20 mmHg or not. If the cuff pressure is lower than 20 mmHg, the process flow advances to step 31 and, after turning off the LED indicating that the measurement process is in progress in step 31, rapid venting of the cuff 2 takes place in step 3. If the cuff pressure is higher than 20 mmHg, pulse wave data $x_i$ is inputted into the MPU 33 in step 24 and the difference between the current value of the pulse wave data $x_i$ and the previous value of the pulse wave data $x_{i-1}$ are compared with a certain value $x_t$. In step 25 it is determined if this difference is greater than this certain value $x_t$ or not.

If the determination result of step 25 is negative, the process flow advances to step 32 and it is determined whether the pulse wave number j has not been updated for 1.5 second. If the pulse wave number j has been updated during that time interval, the current value of the pulse wave data $x_i$ is compared with the maximum pulse wave level $x_{max}$ in step 33. If $x_i > x_{max}$ the maximum pulse wave level $x_{max}$ is updated by the value of $x_i$ in step 34. Conversely, if $x_i < x_{max}$ step 34 is skipped and the process flow advances to step 35. In step 35 the current pulse wave data $x_i$ is compared with the minimum pulse wave level $x_{min}$. If $x_i < x_{min}$ the minimum pulse wave level $x_{min}$ is updated by the value of $x_i$ in step 36. Conversely, if $x_i > x_{min}$ step 36 is skipped and the process flow advances to step 37.

When the updating of the maximum and minimum pulse wave level $x_{max}$ and $x_{min}$ in steps 32 to 36 is completed, the count i is incremented by one in step 37 and the process flow returns to step 23. Thereafter, steps 32 to 37 and steps 23 to 25 are repeated and the updating of the maximum and minimum pulse wave level $x_{max}$ and $x_{min}$ continues until $x_{i-1} - x_i > x_t$ holds or until the next cycle of pulse beat begins.

If it is determined that $x_{i-1} - x_i > x_t$ in step 25, the buzzer 39 is activated in step 26 and extraction of the pulse wave is notified to the user. Then, the difference between the maximum and minimum pulse wave level $x_{max}$ and $x_{min}$ (the amplitude of the pulse wave) $A_j$ is derived in step 27 and stored in the MPU 33. And a blood pressure determination process is conducted in step 28 using this amplitude $A_j$ as a parameter. The blood pressure values may be obtained in step 29 in the same manner as described with reference to FIG. 11.

Upon completion of the determination of the the maximum and minimum pressure level (step 29), the obtained blood pressure values are displayed on the display unit 19 in step 30 and, when the process flow has returned to step 3, the fast vent valve 38 is activated in step 3 to complete the measurement process and get ready for the next measurement (steps 6 and 7).

According to the present embodiment, the air buffer 14 was provided in the casing 21, but it is also possible to provide an air buffer in part of the air cuff 2 itself. Alternatively, it is also possible to eliminate the air buffer 14 as long as a desired rate of venting can be achieved with the slow vent valve 41.

Figure 14:
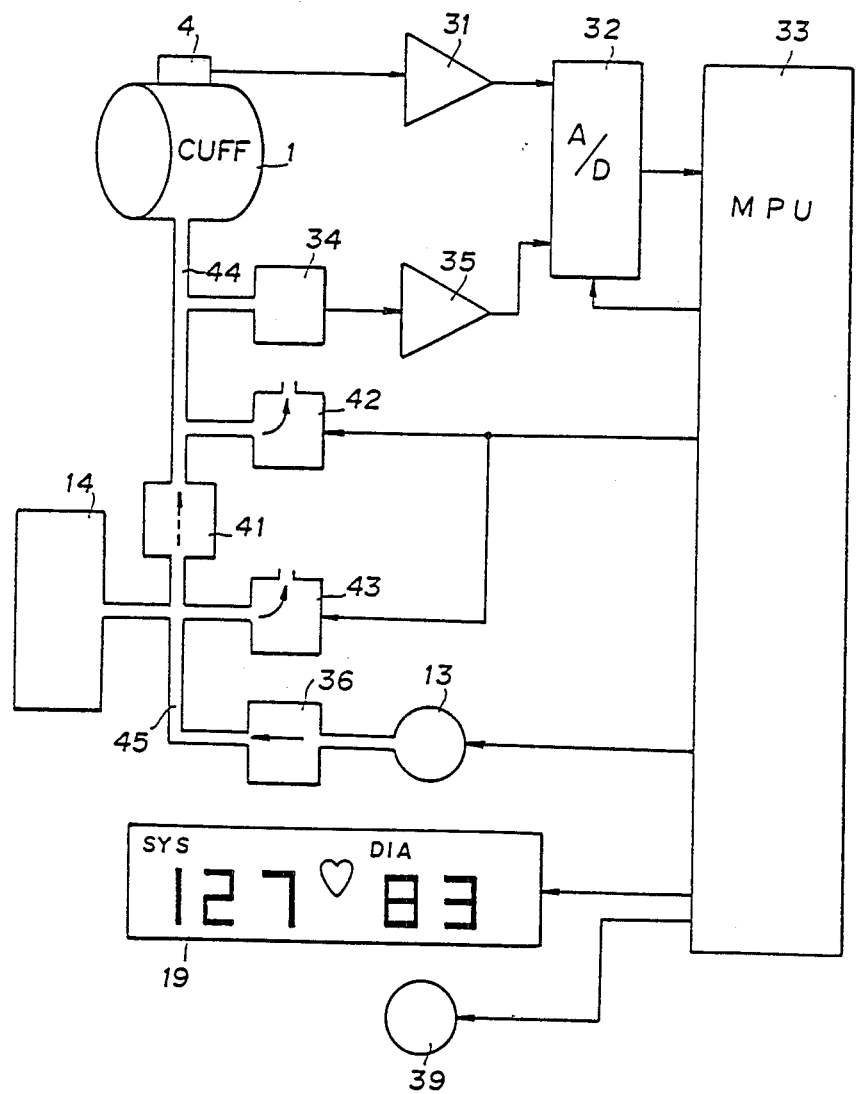
FIG. 14 is a schematic block diagram of a third embodiment of the electronic blood pressure meter according to the present invention.

FIG. 14 shows yet another embodiment of the present invention which is based on a different algorithm for determining the various blood pressure values. In this drawing, the parts corresponding to those in FIG. 4 are denoted by like numerals and their detailed description is omitted.

According to this embodiment, the outlet of an air pump 13 is connected to a conduit 45 by way of a one-way valve 36, and the conduit 45 is connected to another conduit 44 leading to an air cuff 2 by way of a slow vent valve 41. An air buffer 14 and a fast vent valve 43 are connected to the conduit 45 on the side of the air pump 13 while a pressure sensor 34 and another fast vent valve 42 are connected to the other conduit 44 on the side of the air cuff 2.

Figures 15A, 15B:
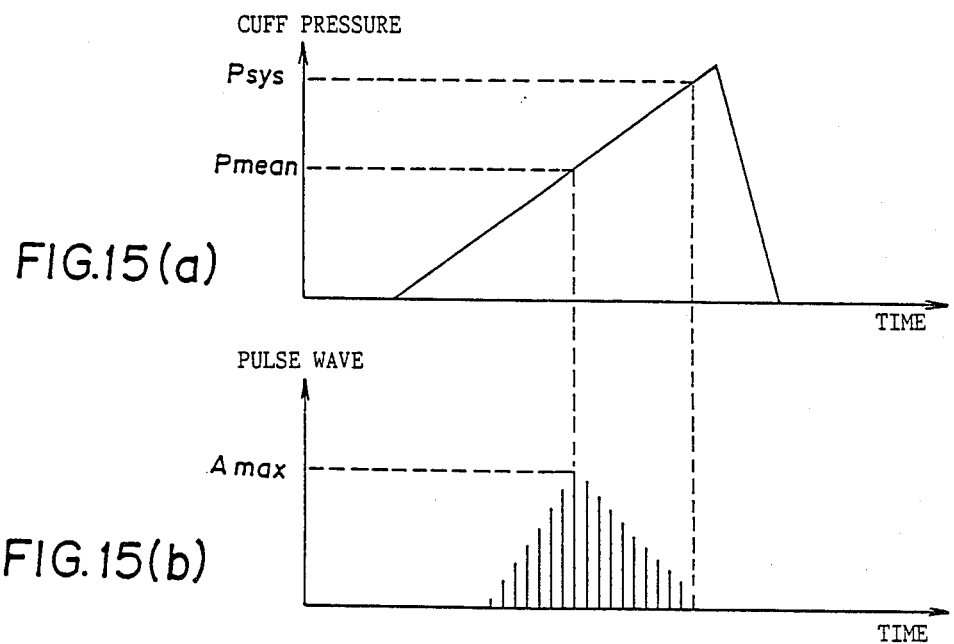
FIG. 15 shows graphs of the cuff pressure and the pulse wave data according to the third embodiment of the electronic blood pressure meter according to the present invention.
Figure 16:
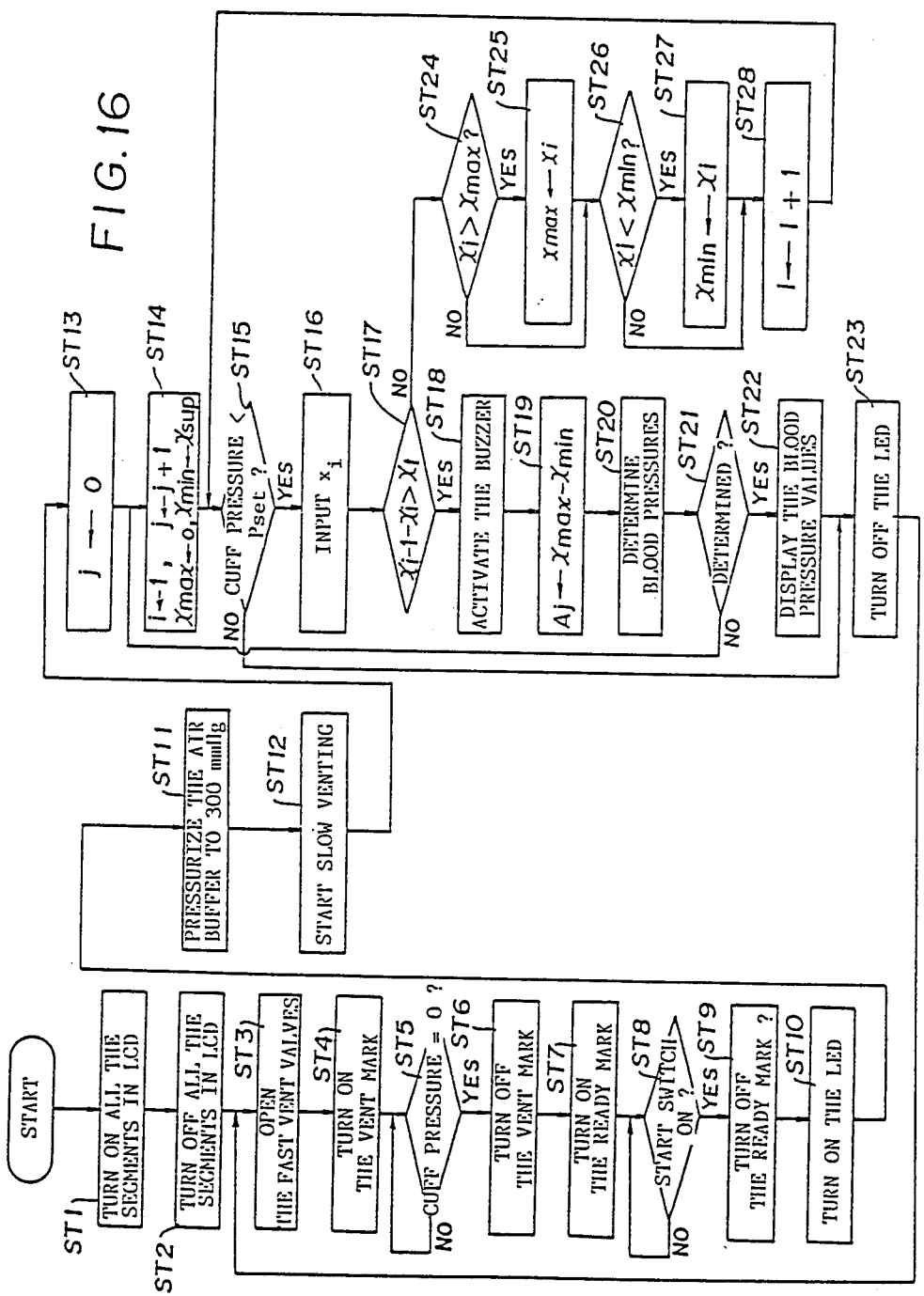
FIG. 16 shows graphs of the cuff pressure and the pulse wave data according to the third embodiment of the electronic blood pressure meter according to the present invention.

FIG. 15 is a flow chart illustrating the action of the embodiment shown in FIG. 14.

Prior to starting a measurement process, a patient put his first finger of his left hand into the cylindrical space of the cuff 2, and the power switch 17 is turned on. This starts off the execution of the program stored in the memory of the MPU 33 and performs a segment check for the display unit 14 by turning on all the segments in the display unit 14 for 1.5 seconds in step 1. Therafter, all the segments are turned off in step 2. In step 3 the fast vent valves 42 and 43 are opened and in step 4 a vent mark (not shown in the drawings) indicating that venting is taking place is lighted. Then it is determined whether the cuff pressure is zero or not in step 5, and the process flow goes into a loop until the cuff pressure drops to zero. When the cuff pressure has dropped to zero, the vent mark is turned off in step 6. Thereafter, a ready mark (indicated as a heart shaped mark in the display unit 19 as shown in FIG. 14) is turned on in step 7 and the system flow goes into a loop until the start switch 18 is turned on in step 8.

When the start switch 18 is turned on, the ready mark on the display unit 19 is turned off in step 9 and an LED indicating that the measurement process is in progress is lighted in step 10. Then, both the fast vent valves 42 and 43 are closed and the air pump 13 is activated until the air pressure in the air buffer 14 reaches 300 mmHg in step 11. This pressure is gradually supplied to the air cuff 2 by opening the slow vent valve 41 which leads to the conduit 44 and the cuff 2 in step 12. As a result, the pressure in the cuff 2 starts rising as shown in FIG. 15 and at the same time the pulse wave detector 26 starts detecting the pulse wave.

In step 13 a pulse wave number j corresponding to the part of the pulse wave at which the amplitude is to be determined is set to zero. In step 14 the count i of a sample counter for one cycle of pulse beat is reset to 1 and the pulse wave number j is incremented by one. At the same time, a maximum pulse wave level $x_{max}$ is set to zero and a minimum pulse wave level $x_{min}$ is set to an upper limit value $x_{sup}$ which is higher than a conceivable maximum value of the pulse wave level.

In step 15, it is determined whether the cuff pressure is higher than lower than a certain predetermined value. If the cuff pressure is higher than the predetermined value, the process flow advances to step 23 and, after the LED indicating that a measurement process is in progress is turned off in step 23, the process flow returns to step 3 where a fast venting with both the fast vent valves 42 and 43 takes place. However, if the cuff pressure is determined to be lower than the predetermined value, pulse wave data $x_i$ is inputted to the MPU 33 in step 16 and the difference between the current value of the pulse wave data $x_i$ and the previous value of the pulse wave data $x_{i-1}$ are compared with a certain value $x_t$ in step 17. This step is for defining the boundaries of each cycle of the pulse beat by sudden changes of the pulse wave level.

If this difference is smaller than this certain value $x_t$ or, in other words, if the determination result of step 17 is negative, the process flow advances to step 24 and the current value of the pulse wave data $x_i$ is compared with the maximum pulse wave level $x_{max}$. If $x_i > x_{max}$ the maximum pulse wave level $x_{max}$ is updated by the value of $x_i$ in step 24. Conversely, if $x_i < x_{max}$ step 25 is skipped and the process flow advances to step 26. In step 26 the current pulse wave data $x_i$ is compared with the minimum pulse wave level $x_{min}$. If $x_i < x_{min}$ the minimum pulse wave level $x_{min}$ is updated by the value of $x_i$ in step 27. Conversely, if $x_i > x_{min}$ step 27 is skipped and the process flow advances to step 28.

When the updating of the maximum and minimum pulse wave level $x_{max}$ and $x_{min}$ in steps 24 to 27 is completed, the count i is incremented by one in step 28 and the process flow returns to step 15. Thereafter, steps 24 to 28 and steps 15 to 17 are repeated and the updating of the maximum and minimum pulse wave level $x_{max}$ and $x_{min}$ continues until $x_{i-1} - x_i > x_t$ holds or until the next cycle of pulse beat begins.

If it is determined that $x_{i-1} - x_i > x_t$ in step 17, the buzzer 39 is activated in step 18 and extraction of the pulse wave is notified to the user. Then, the difference between the maximum and minimum pulse wave level $x_{max}$ and $x_{min}$ (the amplitude of the pulse wave) $A_j$ is derived in step 19 and stored in the MPU 33. And a blood pressure determination process is conducted in step 20 using this amplitude $A_j$ as a parameter. According to this determination process, the maximum value of the pulse wave amplitude $A_j$ is extracted and the cuff pressure at the time point at which the maximum pulse wave amplitude $A_{max}$ is detected is determined as a mean blood pressure $P_{mean}$. Then, the cuff pressure at the time point at which the pulse wave disappears as the cuff pressure is gradually increased is determined as the systolic blood pressure $P_{sys}$. And, the diastolic blood pressure $P_{dia}$ a is determined from the following equation:

$$P_{mean} = P_{dia} + (P_{sys} - P_{dia})/3$$

And, until the diastolic blood pressure $P_{dia}$ is determined, the process flow continues returning from step 21 to step 13 and, after incrementing the pulse wave number j by one in step 13, the blood pressure determination process is continued by deriving the difference between the maximum and minimum pulse wave level $x_{max}$ and $x_{min}$ or the amplitude of the pulse wave) $A_j$ for each cycle of the pulse beat.

Upon completion of the determination of the systolic and diastolic blood pressure levels (step 20), these blood pressure values are displayed on the display unit 19 in step 21 and the LED for indicating that a measurement process is in progress is turned off in step 23. Thereafter, the process flow returns to step 3 where the fast vent valves 42 and 43 are activated again for full venting, and steps 3 to 7 complete the measurement process.

According to this embodiment, the time required for measurement is substantially reduced and the discomfort to the patient whose blood pressure is to be measured can be substantially reduced. Also, the advantage of this embodiment in reducing in the degree of obstructing blood flow is particularly favorable when the blood pressure of a seriously ill person is to be measured.

Figure 17:
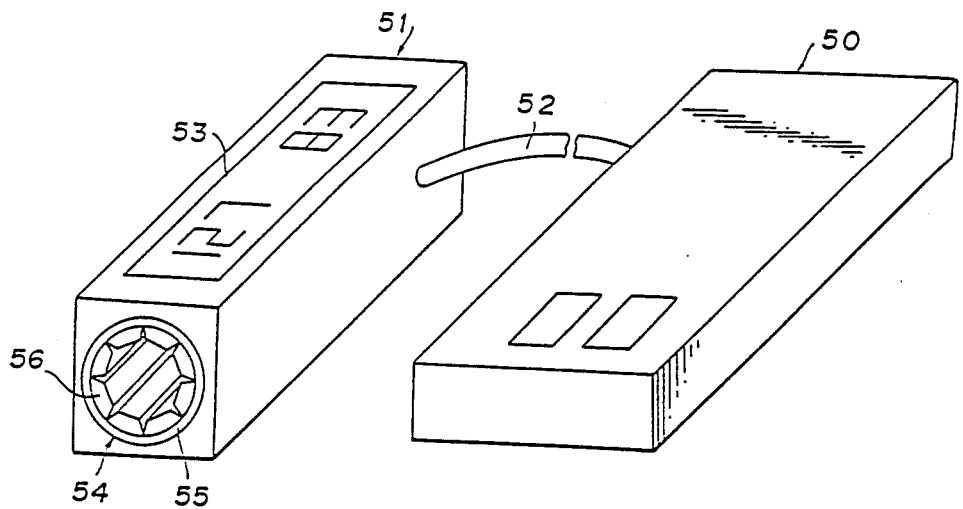

FIG. 17 shows yet another embodiment of the present invention which comprise a main unit 50 and a cuff unit 51 which are built as separate units and mutually connected by electric cables 52. A display unit 53 is provided on the exterior of the cuff unit 51, and a cuff 56 is fitted into a tubular member 55 provided in the cuff unit 51 and is open on one end surface of the casing for the cuff unit 51. The cuff 56 itself may be identical to those described previously.

Although the present invention has been shown and described with reference to the preferred embodiments thereof, it should not be considered as limited thereby. Various possible modifications and alterations could be conceived of by one skilled in the art to any particular embodiment, without departing from the scope of the invention.

What we claim is:

1. A cuff for measuring blood pressure by surrounding a finger of a living body and obstructing the blood in the finger, comprising:
   an airbag having an internal and an external skin, said airbag being sized and adapted to surround said finger and having a certain length defined in a direction along said finger and a certain width defined in a direction around said finger when said airbag is positioned on said finger, said internal and external skins having ends and being contiguously joined at said ends along said length and serving to define an inflatable chamber, said air bag width being sufficient for substantially surrounding said finger, said internal skin being pre-formed into a plurality of adjacent sectioned air chambers, each of said sectioned air chambers extending substantially along the entirety of said airbag length and freely communicating with an adjacent chamber along the entirety of said length, said internal skin being sufficiently flexible such that respective sectioned chambers are adapted to be inflated individually with respect to other of said sectioned chambers while said airbag is positioned on said finger.

2. A cuff for measuring blood pressure as defined in claim 1, wherein the internal skin is provided with a plurality of bulges of a substantially trapezoidal shape defining the corresponding air chambers, wherein the internal skin defines a shorter side between the two parallel sides of each of the trapezoidal shaped bulges.

3. A cuff for measuring blood pressure as defined in claim 1, wherein the internal skin is provided with a plurality of bulges of a substantially semicircular shape defining the corresponding air chambers, wherein the internal skin defines a circular portion of each of the semicircular shaped bulges.

4. A cuff for measuring blood pressure as defined in claim 2 or 3, wherein the external skin is substantially flat.

5. A cuff for measuring blood pressure as defined in claim 2 or 3, wherein the external skin is substantially symmetric to the inner skin in shape.

6. An electronic blood pressure meter and cuff combination for measuring blood pressure by surrounding a finger of a living body and obstructing the blood in the finger, comprising:
   an airbag having an internal and an external skin, said airbag being sized and adapted to surround said finger and having a certain length defined in a direction along said finger and a certain width defined in a direction around said finger when said airbag is positioned on said finger, said internal and external skins having ends and being contiguously joined at said ends along said length and serving to define an inflatable chamber, said air bag width being sufficient for substantially surrounding said finger, said internal skin being pre-formed into a plurality of adjacent sectioned air chambers, each of said sectioned air chambers extending substantially along the entirety of said airbag length and freely communicating with an adjacent chamber along the entirety of said length, said internal skin being sufficiently flexible such that respective sectioned chambers are adapted to be inflated individually with respect to other of said sectioned chambers while said airbag is positioned on said finger, at least one chamber being recessed relative to at least one adjacent chamber for accommodating at least one artery sensor thereon.

* * * * *